US009795683B2

(12) United States Patent
Jain et al.

(10) Patent No.: US 9,795,683 B2
(45) Date of Patent: *Oct. 24, 2017

(54) GLYCOPOLYSIALYLATION OF NON-BLOOD COAGULATION PROTEINS

(75) Inventors: Sanjay Jain, London (GB); Gregory Gregoriadis, London (GB); Archana Dwivedi, London (GB); Srijit Nath, London (GB); Juergen Siekmann, Vienna (AT); Stefan Haider, Prinzersdorf (AT); Hanspeter Rottensteiner, Vienna (AT); Peter Turecek, Klosterneuburg (AT)

(73) Assignees: Lipoxen Technologies Limited, London (GB); Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 355 days.

This patent is subject to a terminal disclaimer.

(21) Appl. No.: 12/843,284

(22) Filed: Jul. 26, 2010

(65) Prior Publication Data

US 2011/0027350 A1 Feb. 3, 2011

Related U.S. Application Data (60) Provisional application No. 61/228,828, filed on Jul. 27, 2009, provisional application No. 61/347,136, filed on May 21, 2010.

(51) Int. Cl.
*A61K 9/127* (2006.01)
*A61K 47/48* (2006.01)

(52) U.S. Cl.
CPC .... *A61K 47/4823* (2013.01); *A61K 47/48215* (2013.01)

(58) Field of Classification Search
CPC .......... A61K 47/48215; A61K 47/4823; A61K 47/48238; A61K 38/37; A61K 38/4846; A61K 47/48023; A61K 36/73; A61K 38/21; A23V 2002/00; A23V 2200/308; A23V 2200/314; A23V 2250/21; C12Y 304/21021; C12Y 304/21022; C07K 1/1077; C07K 14/755; C07K 1/1075; C08B 37/0006; C12N 9/6437; C12N 9/644; C12N 9/96; A61B 17/29; A61B 2017/2934; A61B 10/06; A61B 17/2909; A61B 2017/0046; A61B 2017/2837; A61B 2017/291; A61B 2017/292; A61B 2017/2936; A61B 90/03; A23L 33/105; A23L 3/06; A23L 3/362; C01B 31/04; G01N 27/4045; G01N 2440/00; G01N 33/6842; G01N 33/6857; G01N 27/3335; G01N 33/588; A23N 12/04; B01J 8/10; B01J 13/0004; B01J 13/02; B01J 13/22; B65G 2207/24; H05B 7/06; Y10T 29/417; B82Y 20/00; B82Y 40/00; C09K 11/883; C12P 19/02; C12P 19/12; C12P 2203/00; C12P 7/52; E02F 3/885; E02F 3/90; E02F 3/905; E02F 7/065; E02F 7/10; E21C 50/00; F16D 65/543; F16D 65/56; F16D 65/567; G02B 5/3083; G02F 1/13363; G02F 2001/133631; H01L 21/02474; H01L 21/02477; H01L 31/035218; H01L 33/28; H01L 33/44; Y02E 50/17; Y02E 50/343; Y10S 977/89; Y10S 977/95

See application file for complete search history.

(56) References Cited

U.S. PATENT DOCUMENTS

| 4,179,337 A | * | 12/1979 | Davis et al. ................ 435/181 |
| 4,757,006 A | | 7/1988 | Toole, Jr. et al. |
| 4,966,999 A | | 10/1990 | Coughlin et al. |
| 4,970,300 A | | 11/1990 | Fulton et al. |
| 5,122,614 A | * | 6/1992 | Zalipsky ...................... 548/520 |
| 5,153,265 A | | 10/1992 | Shadle et al. |
| 5,198,349 A | | 3/1993 | Kaufman |

(Continued)

FOREIGN PATENT DOCUMENTS

| CA | 2647314 A1 | 11/2007 |
| EP | 0306968 A2 | 3/1989 |
| EP | 0605963 A2 | 7/1994 |
| EP | 1258497 A2 | 11/2002 |
| EP | 1260582 A1 | 11/2002 |
| EP | 1 681 303 A1 | 7/2006 |
| JP | H03503759 A | 8/1991 |
| JP | 2003533537 A | 11/2003 |

(Continued)

OTHER PUBLICATIONS

Gregoriadis et al. (2005) Intl. J. Pharm. 300(1-2): 125-130.*

(Continued)

*Primary Examiner* — Lisa J Hobbs
(74) *Attorney, Agent, or Firm* — Morgan, Lewis & Bockius LLP (57) ABSTRACT

A water soluble polymer, in particular polysialic acid (PSA) or a modified PSA (mPSA), is conjugated to an oxidized carbohydrate moiety of a glycoprotein other than a blood coagulation protein or to a ganglioside or drug delivery system by contacting the oxidized carbohydrate moiety with the water soluble polymer, wherein said water soluble polymer contains an aminooxy group and an oxime linkage is formed between the oxidized carbohydrate moiety and the aminooxy group on the water soluble polymer or wherein said water soluble polymer contains a hydrazide group and a hydrazone linkage is formed between the oxidized carbohydrate moiety and the hydrazide group on the water soluble polymer. Conjugates of aminooxy- or hydrazide-water soluble polymer, such as PSA and mPSA, are thus obtained in which the PSA or mPSA is attached via a carbohydrate moiety.

11 Claims, 2 Drawing Sheets

(56) References Cited

U.S. PATENT DOCUMENTS

| | | | |
|---|---|---|---|
| 5,198,493 A | 3/1993 | Holmberg et al. | |
| 5,250,421 A | 10/1993 | Kaufman et al. | |
| 5,298,643 A * | 3/1994 | Greenwald | 558/6 |
| 5,492,821 A | 2/1996 | Callstrom et al. | |
| 5,621,039 A | 4/1997 | Hallahan et al. | |
| 5,733,873 A | 3/1998 | Osterberg et al. | |
| 5,919,766 A | 7/1999 | Osterberg et al. | |
| 5,969,040 A | 10/1999 | Hallahan et al. | |
| 6,037,452 A * | 3/2000 | Minamino et al. | 530/383 |
| 6,048,720 A | 4/2000 | Dalborg et al. | |
| 6,183,738 B1 | 2/2001 | Clark | |
| 6,586,398 B1 | 7/2003 | Kinstler et al. | |
| 6,692,931 B1 | 2/2004 | Reutter et al. | |
| 6,743,908 B2 | 6/2004 | Filpula et al. | |
| 6,806,063 B2 | 10/2004 | Pedersen et al. | |
| 6,872,393 B2 | 3/2005 | Whitlow et al. | |
| 6,913,915 B2 | 7/2005 | Ensor et al. | |
| 7,118,737 B2 | 10/2006 | Kochendoerfer et al. | |
| 7,199,223 B2 * | 4/2007 | Bossard et al. | 530/383 |
| 7,230,081 B1 | 6/2007 | Jensen et al. | |
| 7,338,788 B2 | 3/2008 | Pedersen et al. | |
| 7,645,860 B2 | 1/2010 | Turecek et al. | |
| 7,875,708 B2 * | 1/2011 | Jain et al. | 536/17.2 |
| 2002/0110535 A1 | 8/2002 | Jones | |
| 2002/0137125 A1 | 9/2002 | Zhu | |
| 2003/0143596 A1 | 7/2003 | Bentley et al. | |
| 2004/0063911 A1 | 4/2004 | DeFrees et al. | |
| 2004/0126838 A1 | 7/2004 | DeFrees et al. | |
| 2004/0137557 A1 | 7/2004 | DeFrees et al. | |
| 2004/0142856 A1 | 7/2004 | DeFrees et al. | |
| 2004/0235734 A1 | 11/2004 | Bossard et al. | |
| 2005/0106658 A1 | 5/2005 | DeFrees et al. | |
| 2006/0019877 A1 | 1/2006 | Conradt et al. | |
| 2006/0088906 A1 | 4/2006 | DeFrees et al. | |
| 2006/0286634 A1 | 12/2006 | Kingsman et al. | |
| 2007/0105755 A1 | 5/2007 | DeFrees et al. | |
| 2007/0244301 A1 | 10/2007 | Siekmann et al. | |
| 2008/0146771 A1 | 6/2008 | Kozlowski et al. | |
| 2008/0260755 A1 | 10/2008 | Metzner et al. | |
| 2009/0076237 A1 * | 3/2009 | Turecek et al. | 527/207 |

FOREIGN PATENT DOCUMENTS

| | | |
|---|---|---|
| JP | 2005232172 A | 9/2005 |
| JP | 2006505635 A | 2/2006 |
| JP | 2006511635 A | 4/2006 |
| JP | 2006516534 A | 7/2006 |
| JP | 2007527891 A | 10/2007 |
| JP | 2008510024 A | 4/2008 |
| JP | 2008531764 A | 8/2008 |
| WO | WO-91/09122 A1 | 6/1991 |
| WO | WO-92/16555 A1 | 10/1992 |
| WO | WO-94/05332 A2 | 3/1994 |
| WO | WO-94/15625 A1 | 7/1994 |
| WO | WO 9415625 A1 * | 7/1994 |
| WO | WO-94/28024 A1 | 12/1994 |
| WO | WO-94/29370 A1 | 12/1994 |
| WO | WO-95/01804 A1 | 1/1995 |
| WO | WO-96/40662 A2 | 12/1996 |
| WO | WO-96/40731 A1 | 12/1996 |
| WO | WO-96/41813 A2 | 12/1996 |
| WO | WO-97/11957 A1 | 4/1997 |
| WO | WO-99/28455 A1 | 6/1999 |
| WO | WO-99/32134 A1 | 7/1999 |
| WO | WO-00/12587 A2 | 3/2000 |
| WO | WO-00/23114 A2 | 4/2000 |
| WO | WO-00/48635 A1 | 8/2000 |
| WO | WO-01/82943 A2 | 11/2001 |
| WO | WO-01/83725 A1 | 11/2001 |
| WO | WO-01/87922 A2 | 11/2001 |
| WO | WO-02/02764 A2 | 1/2002 |
| WO | WO-02/22776 A2 | 3/2002 |
| WO | WO-02/29025 A2 | 4/2002 |
| WO | WO-02/077218 A1 | 10/2002 |
| WO | WO-03/031464 A2 | 4/2003 |
| WO | WO-03/045980 A2 | 6/2003 |
| WO | WO-03/046150 A2 | 6/2003 |
| WO | WO-2004/000366 A1 | 12/2003 |
| WO | WO-2004/014424 A1 | 2/2004 |
| WO | WO-2004/030617 A2 | 4/2004 |
| WO | WO-2004/060965 A | 7/2004 |
| WO | WO-2004/075923 A2 | 9/2004 |
| WO | WO-2004/089280 A2 | 10/2004 |
| WO | WO-2004/108070 A2 | 12/2004 |
| WO | WO-2005/014024 A2 | 2/2005 |
| WO | WO-2005/014035 A2 | 2/2005 |
| WO | WO-2005/016973 A1 | 2/2005 |
| WO | WO-2005/016974 A1 | 2/2005 |
| WO | WO 2005014024 A2 * | 2/2005 |
| WO | WO-2005/055950 A2 | 6/2005 |
| WO | WO-2005/070138 A2 | 8/2005 |
| WO | WO-2006/013202 A2 | 2/2006 |
| WO | WO-2006/016168 A2 | 2/2006 |
| WO | WO-2006/020372 A2 | 2/2006 |
| WO | WO-2006/053299 A2 | 5/2006 |
| WO | WO-2006/071801 A2 | 7/2006 |
| WO | WO-2006/074279 A1 | 7/2006 |
| WO | WO-2006/127896 A2 | 11/2006 |
| WO | WO-2006/134173 A2 | 12/2006 |
| WO | WO-2007/022784 A2 | 3/2007 |
| WO | WO-2007/076062 A2 | 7/2007 |
| WO | WO-2007/140282 A1 | 12/2007 |
| WO | WO-2008/012525 A1 | 1/2008 |
| WO | WO-2008/012528 A1 | 1/2008 |
| WO | WO-2008/012540 A1 | 1/2008 |
| WO | WO-2008/012542 A2 | 1/2008 |
| WO | WO-2008/025856 A2 | 3/2008 |
| WO | WO-2008/035373 A2 | 3/2008 |
| WO | WO 2008025856 A2 * | 3/2008 |
| WO | WO-2008/057683 A2 | 5/2008 |
| WO | WO-2008/074032 A1 | 6/2008 |
| WO | WO-2008/081024 A1 | 7/2008 |
| WO | WO-2008/089403 A2 | 7/2008 |
| WO | WO-2008/119815 A1 | 10/2008 |
| WO | WO-2009/000522 A1 | 12/2008 |
| WO | WO-2009/006620 A1 | 1/2009 |
| WO | WO-2009/047500 A1 | 4/2009 |
| WO | WO-2009/089396 A2 | 7/2009 |
| WO | WO-2009/108806 A1 | 9/2009 |
| WO | WO-2009/130602 A2 | 10/2009 |
| WO | WO-2009/141418 A1 | 11/2009 |
| WO | WO-2009/141433 A1 | 11/2009 |
| WO | WO-2009/149303 A1 | 12/2009 |
| WO | WO-2010/010324 A1 | 1/2010 |
| WO | WO-2010/062768 A1 | 6/2010 |
| WO | WO-2010/083536 A1 | 7/2010 |
| WO | WO-2010/100430 A1 | 9/2010 |
| WO | WO-2010/102886 A1 | 9/2010 |
| WO | WO-2010/120365 A2 | 10/2010 |
| WO | WO-2010/131015 A1 | 11/2010 |
| WO | WO-2011/012850 A2 | 2/2011 |
| WO | WO-2011/014890 A1 | 2/2011 |
| WO | WO-2011/017055 A2 | 2/2011 |
| WO | WO-2011/018496 A2 | 2/2011 |
| WO | WO-2011/037896 A2 | 3/2011 |
| WO | WO-2011/064247 A1 | 6/2011 |
| WO | WO-2011/101242 A1 | 8/2011 |
| WO | WO-2011/101267 A1 | 8/2011 |
| WO | WO-2011/135307 A1 | 11/2011 |
| WO | WO-2011/135308 A1 | 11/2011 |
| WO | WO-2012/068134 A1 | 5/2012 |
| WO | WO-2013/009627 A2 | 1/2013 |

OTHER PUBLICATIONS

Abuchowski et al., Cancer therapy with chemically modified enzymes. I. Antitumor properties of polyethylene glycol-asparaginase conjugates. *Cancer Biochem. Biophys.* 7: 175-86 (1984).

Baxter announces collaborations to develop longer acting forms of blood clotting factors. *Baxter News* (online), Sep. 29, 2005.

Bi et al., Target disruption of the mouse factor VIII gene produces a model of Haemophilia A. *Nat. Genet.* 10: 119-21 (1995).

(56) References Cited

OTHER PUBLICATIONS

Caliceti et al., Pharmacokinetics of pegylated interferons: What is misleading? *Digest. Liver Dis.* 36(Suppl. 3): S334-9 (2004).
Cordes et al., Nucleophilic catalysis of semicarbazone formation by anilines. *J. Am. Chem. Soc.*, 84: 826-31 (1962).
Dirksen et al., Nucleophilic catalysis of hydrazone formation and transimination: Implications for dynamic covalent chemistry. *J. Am. Chem. Soc.*, 128: 15602-3 (2006).
Dirksen et al., Nucleophilic catalysis of oxime ligation. *Ange. Chem. Int. Ed.*, 45(45): 7581-4 (2006).
Dirksen et al., Rapid oxime and hydrazone ligations with aromatic aldehyres for biomolecular labeling. *Bioconj. Chem.*, 19(12): 2543-8 (2008).
Gregoriadis et al., Improving the therapeutic efficacy of peptides and proteins: A role for polysialic acids. *Int. J. Pharmaceut.*, 300(1-2): 125-30 (2005).
Harris et al., Effect of pegylation on pharmaceuticals. *Nat. Rev. Drug Discovery.* 2: 214-21 (2003).
Jain et al., Polysialylation: The natural way to improve the stability and pharmacokinestics of protein and peptide drugs <<http://www.lipoxen.co.uk/media/48760/dds%20and%20s%20pp3-9.pdf>>, dds &s, 4(1): 3-9 (2004).
Jiang et al., Chemistry for pegylation of protein and peptide molecules, *Chin. J. Organ. Chem.*, 23(12): 1340-7 (2003).—English Abstract.
Kohler, Aniline: A catalyst for sialic acid detection. *ChemBioChem*, 10: 2147-50 (2009).
Kozlowski et al., Development of pegylated interferons for the treatment of chronic Hepatitis C. *BioDrugs.* 15(7): 419-29 (2001).
Lees et al., Versatile and efficient synthesis of protein-polysaccharide conjugate vaccines using aminooxy reagents and oxime chemistry. *Vaccine*, 24(6): 716-29 (2006).
Nektar Advanced PEGylation Catalog 2005-2006, p. 30 (2005).
Nektar Advanced PEGylation Price List 2005-2006, p. 11 (2005).
NOF Corporation DDS Catalogue, p. 58 (2005).
Roberts et a., Chemistry for peptide and protein pegylation *Adv. Drug Del. Rev.* 54: 459-76 (2002).
Rosen et al., Assay of factor VIII: C with a chromogenic substrate. *Scand J. Haematot* 33(Suppl. 40): 139-45 (1984).
Rostin et al., B-domain deleted recombinant coagulation factor VIII modified with monomethoxy polyethylene glycol. *Bioconjugate Chem.* 11: 387-96 (2000).
Saenko et al., Strategies towards a longer acting factor VIII. *Haemophilia.* 12: 42-51 (2006).
Sakuragawa et al., Studies on the stability of factor VIII modified by polyethylene glycol. *Acta Med. Biol.* 36: 1-5 (1988).
Seffernick et al., Melamine deaminase and atrazine chlorohydrolase: 98% identical but functionally different. *J. Bacteriology.* 2405-10 (2001).
Severs et al., Characterization of PEGylated factor VIII molecules. *Blood.* 108: 11-12 (2006). Abstract.
Study shows molecular size and structure of PEG interferon molecules, as used in pegintron(R), affect antiviral activity in vitro. *Hispanic PR Wire*, Oct. 28, 2003.
Thygesen et al., Nucleophilic catalysis of carbohydrate oxime formation by anilines. *J. Org. Chem.*, 75: 1752-5 (2010).
Tsubery et al., Prolonging the action of protein and peptide drugs by a novel approach of reversible polyethylene glycol modification. *J. Biol. Chem.* 279(37): 38118-24 (2004).
Tsutsumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA.* 97: 8548-53 (2000).
Urrutigoity et al., Biocatalysis in organic solvents with a polymer-bound horseradish peroxidase. *Biocatalysis.* 2: 145-9 (1989).
Veronese et al., Bioconjugation in pharmaceutical chemistry. *IL Farmaco.* 54: 497-516 (1999).
Wells et al., Additivity of mutational effects in proteins. *Biochemistry.* 29(37): 8509-17 (1990).
Wilchek et al., Labeling glycoconjugates with hydrazide reagents. *Methods Enzymol.* 138: 429-42 (1987).
Zalipsky et al., Hydrazide derivatives of poly(ethylene glycol) and their bioconjugates. Poly(ethylene glycol) Chemistry and Biological Applications. Chapter 21, pp. 318-341 (1997).
Zeng et al., High-efficency labeling of sialylated glycoproteins on living cells. *Nat. Methods*, 6(3): 207-9 (2009).
Great Britain Search Report and Written Opinion, GB-1012482.4, dated Nov. 24, 2010.
International Search Report and Written Opinion of the International Searching Authority, PCT/US2007/007560, European Patent Office, dated Sep. 18, 2007.
International Preliminary Report on Patentability, PCT/US2007/007560, dated Sep. 30, 2008.
International Search Report and Written Opinion of the International Searching Authority, PCT/US2009/052103, European Patent Office, dated Feb. 12, 2010.
International Preliminary Report on Patentability, PCT/US2009/052103, dated Feb. 1, 2011.
International Search Report and Written Opinion, PCT/US2010/043242, dated Feb. 10, 2011.
International Preliminary Report on Patentability, PCT/US2010/043242, dated Jan. 31, 2012.
International Search Report and Written Opinion of the International Searching Authority, PCT/GB2010/001422, European Patent Office, dated Feb. 4, 2011.
International Preliminary Report on Patentability, PCT/GB2010/001422, dated Jan. 31, 2012.
International Search Report and Written Opinion of the International Searching Authority, PCT/US2011/045873, European Patent Office, dated Nov. 24, 2011.
International Preliminary Report on Patentability, PCT/US2011/045873, dated Feb. 5, 2013.
Boturyn et al., Synthesis of fluorescent probes for the detection of abasic sites in DNA, *Tetrahedron*, 53(15):5485-92 (1997).
Fernandes et al., Polysialylated asparaginase: preparation, activity and pharmacokinetics, *Biochim. Biophys. Acta*, 1341(1):26-34 (1997).
Gregoriadis, Targeting of drugs, *Nature*, 265(5593):407-11 (1977).
Gregoriadis, The physiology of the liposome, *NIPS*, 4:146-51 (1989).
Heredia et al., Aminooxy end-functionalized polymers synthesized by ATRP for chemoselective conjugation to proteins, *Macromolecules*, 40:4772-9 (2007).
Kang et al., Asymmetric synthesis of N-acetylneuraminic acid, *Chem. Commun.*, 227-8 (2000).
Kubler-Kielb et al., A new method for conjugation of carbohydrates to proteins using an aminooxy-thiol heterobifunctional linker, *J. Org. Chem.*, 70(17):6987-90 (2005).
Lehninger, Chapter 4, The Amino Acid Building Blocks of Protein, pp. 71-7, IN: Biochemistry, 2nd ed., New York: Worth Publishers Inc. (1975).
Malaprade, Analytical application, *Bull. Soc. Chim.* France, 43:683-96 (1928). [French only].
Marko et al., Efficient, aerobic, ruthenium-catalyzed oxidation of alcohols into aldehydes and ketones, *J. Am. Chem. Soc.*, 119:12261-2 (1997).
Peri et al., Chemo- and stereoselective glycosylation of hydroxylamino derivatives: a versatile approach to glycoconjugates, *Tetrahedron*, 54:12269-78 (1998).
Ress et al., Sialic acid donors: chemical synthesis and glycosylation, *Curr. Org. Synth.*, 1:31-46 (2004).
Rothfus et al., IV. The priodate oxidation of glycopeptides from Human gamm-globulin, *J. Biol. Chem.*, 238(4):1402-10 (1963).
Toyokuni et al., Synthesis of a new heterobifunctional linker, N-[4-aminooxy)butyl]maleimide, for facile access to a thiol-reactive $^{18}$F-labeling agent, *Bioconjugate Chem.*, 14:1253-9 (2003).
Van Lenten et al., Studies on the chemical and enzymatic modification of glycoproteins, *J. Biol. Chem.*, 246(6):1889-94 (1971).
Butenas et al., Potency and mass of factor VIII and FVIII products. *Haemophilia*, 15: 63-42 (2009).
Declaration of Juergen Siekmann, Ph.D., dated Jun. 29, 2009.
Declaration of Juergen Siekmann, Ph.D., dated Apr. 4, 2013.

(56) References Cited

OTHER PUBLICATIONS

El-Maarri et al., Functional analysis of the factor VIII B domain. 34th Hemophilia Symposium, pp. 324-37 (2005).
Geoghegan et al., Periodate inactivation of ovotransferrin and human serum transferrin. *J. Biol. Chem.* 255(27): 11429-34 (1980).
Lenting et al., Factor VIII and von Willebrand factor—too sweet for their own good. *Haemophilia*, 16(Suppl. 5): 194-9 (2010).
Lenting et al., The life cycle of coagulation factor VIII in view of its structure and function. Blood, 92(11): 3983-96 (1998).
Mazsaroff et al., Quantitative comparison of global carbohydrate structures of glycoproteins using LC-MS and in-source fragmentation. *Anal. Chem.* 69(13): 2517-24 (1997).
Parti et al., In vitro stability of recombinant human factor VIII (Recombinate®). *Haemophilia*, 6: 513-22 (2000).

\* cited by examiner

GLYCOPOLYSIALYLATION OF NON-BLOOD COAGULATION PROTEINS

FIELD OF THE INVENTION

The present invention relates to materials and methods for conjugating water soluble polymers, in particular polysialic acid, to carbohydrate-containing compounds, in particular glycoproteins other than a blood coagulation proteins, and to the conjugates obtained.

BACKGROUND OF THE INVENTION

Conjugation of polypeptide drugs such as by PEGylation or polysialylation protects them from degradation in the blood circulation and thus improves their pharmacodynamic and pharmacokinetic profiles (Harris and Chess, Nat Rev Drug Discov. 2003; 2:214-21). The PEGylation process attaches repeating units of ethylene glycol (polyethylene glycol (PEG)) to a polypeptide drug. PEG molecules have a large hydrodynamic volume (5-10 times the size of globular proteins), are highly water soluble and hydrated, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. The first PEGylated drugs were approved by the FDA in the early 1990s. Since then, the FDA has approved several PEGylated drugs for oral, injectable, and topical administration.

Sialic acids (also called N-acetyl neuraminic acids) and polysialic acids are found widely distributed in animal tissues and to a lesser extent in other species ranging from plants and fungi to yeasts and bacteria, mostly in glycoproteins and gangliosides.

The abbreviation "PSA" used herein refers to the term "polysialic acid". Similarly, the term "mPSA" used herein refers to the term "modified polysialic acid".

PSAs consist of polymers (generally homopolymers) of N-acetylneuraminic acid. The secondary amino group normally bears an acetyl group, but it may instead bear a glycolyl group. Possible substituents on the hydroxyl groups include acetyl, lactyl, ethyl, sulfate, and phosphate groups.

N-Acetylneuraminic acid
Neu5Ac

Structure of Sialic Acid (N-Acetylneuraminic Acid)

PSAs and mPSAs generally comprise linear polymers consisting essentially of N-acetylneuraminic acid moieties linked by 2,8- or 2,9-glycosidic linkages or combinations of these (e.g. alternating 2,8- and 2,9-linkages). In particularly preferred PSAs and mPSAs, the glycosidic linkages are α-2,8. Such PSAs and mPSAs are conveniently derived from colominic acids, and are referred to herein as "CAs" and "mCAs". Typical PSAs and mPSAs comprise at least 2, preferably at least 5, more preferably at least 10 and most preferably at least 20 N-acetylneuraminic acid moieties. Thus, they may comprise from 5 to 500 N-acetylneuraminic acid moieties, preferably from 10 to 300 N-acetylneuraminic acid moieties. PSAs and CAs can be polymers comprising different sugar moieties. They can be copolymers. PSAs and CAs preferably are essentially free of sugar moieties other than N-acetylneuraminic acid. PSAs and CAs preferably comprise at least 90%, more preferably at least 95% and most preferably at least 98% N-acetylneuraminic acid moieties.

Where PSAs and CAs comprise moieties other than N-acetylneuraminic acid (as, for example in mPSAs and mCAs) these are preferably located at one or both of the ends of the polymer chain. Such "other" moieties may, for example, be moieties derived from terminal N-acetylneuraminic acid moieties by oxidation or reduction.

For example, WO-A-0187922 describes such mPSAs and mCAs in which the non-reducing terminal N-acetylneuraminic acid unit is converted to an aldehyde group by reaction with sodium periodate. Additionally, WO 2005/016974 describes such mPSAs and mCAs in which the reducing terminal N-acetylneuraminic acid unit is subjected to reduction to reductively open the ring at the reducing terminal N-acetylneuraminic acid unit, whereby a vicinal diol group is formed, followed by oxidation to convert the vicinal diol group to an aldehyde group.

Sialic acid rich glycoproteins bind selectin in humans and other organisms. They play an important role in human influenza infections. For example, sialic acid can hide mannose antigens on the surface of host cells or bacteria from mannose-binding lectin. This prevents activation of complement. Sialic acids also hide the penultimate galactose residue thus preventing rapid clearance of the glycoprotein by the galactose receptor on the hepatic parenchymal cells.

Structure of Colominic Acid (Homopolymer of N-Acetylneuraminic Acid)

CAs are produced, inter alia, by particular strains of *Escherichia coli* possessing the K1 antigen. CAs have many physiological functions. They are important as a raw material for drugs and cosmetics.

Comparative studies in vivo with polysialylated and unmodified asparaginase revealed that polysialylation increased the half-life of the enzyme (Fernandes and Gregoriadis, Biochimica Biophysica Acta 1341: 26-34, 1997).

The preparation of conjugates by forming a covalent linkage between the water soluble polymer and the therapeutic protein can be carried out by a variety of chemical methods. One approach for coupling PSA to therapeutic proteins is the conjugation of the polymers via the carbohydrate moieties of the protein. Vicinal hydroxyl (OH) groups of carbohydrates in proteins can be easily oxidized with sodium periodate ($NaIO_4$) to form active aldehyde groups (Rothfus and Smith, J Biol Chem 1963; 238:1402-10; van Lenten and Ashwell, J Biol Chem 1971; 246:1889-94). Subsequently the polymer can be coupled to the aldehyde groups of the carbohydrate by use of reagents containing, for example, an active hydrazide group (Wilchek M and Bayer E A, Methods Enzymol 1987; 138:429-42). A more recent technology is the use of reagents containing aminooxy groups which react with aldehydes to form oxime linkages (WO 96/40662, WO2008/025856).

Additional examples describing conjugation of a PSA to a therapeutic protein are described in US Publication No. 2009/0076237 which teaches the oxidation of rFVIII and subsequent coupling to PSA and other water soluble polymers (e.g. PEG, HES, dextran) using hydrazide chemistry; WO 2008/025856 which teaches oxidation of different coagulation factors, e.g. rFIX, FVIII and FVIIa and subsequent coupling to a polymer, e.g. PEG.

Recently, an improved method was described comprising mild periodate oxidation of sialic acids to generate aldehydes followed by reaction with an aminooxy group containing reagent in the presence of catalytic amounts of aniline (Dirksen A and Dawson P E, Bioconjugate Chem. 2008; 19, 2543-8; and Zeng Y et al., Nature Methods 2009; 6:207-9). The aniline catalysis dramatically accelerates the oxime ligation, allowing the use of very low concentrations of reagents.

Notwithstanding the methods available of conjugating water soluble polymers to therapeutic proteins, there remains a need to develop materials and methods for conjugating water soluble polymers to carbohydrate-containing compounds other than blood coagulation proteins that improve the compound's pharmacodynamic and/or pharmacokinetic properties while minimizing the costs associated with the various reagents.

SUMMARY OF THE INVENTION

The present invention provides materials and methods for conjugating a water soluble polymer to a carbohydrate-containing compound other than a blood coagulation protein that improve the compound's pharmacodynamic and/or pharmacokinetic properties while minimizing the costs associated with the various reagents.

In one embodiment of the invention there is provided a method of conjugating a water soluble polymer to an oxidized carbohydrate moiety of a carbohydrate-containing compound other than a blood coagulation protein, comprising contacting the oxidized carbohydrate moiety with water soluble polymer under conditions that allow conjugation, wherein said water soluble polymer contains an aminooxy group and an oxime linkage is formed between the oxidized carbohydrate moiety and the aminooxy group on the water soluble polymer, or wherein said water soluble polymer contains a hydrazide group and a hydrazone linkage is formed between the oxidized carbohydrate moiety and the hydrazide group on the water soluble polymer. The compound may be (1) a glycoprotein other than a blood coagulation protein, (2) a ganglioside, or (3) a drug delivery system comprising a carbohydrate group.

The carbohydrate moiety may be oxidized using a sugar-specific oxidizing enzyme or by incubation with a buffer comprising an oxidizing agent selected from sodium periodate ($NaIO_4$), lead tetraacetate ($Pb(OAc)_4$) and potassium perruthenate ($KRuO_4$).

The carbohydrate moiety may be oxidized at a sialic acid, mannose, galactose or glucose residue.

The water-soluble polymer used in the invention can be, but is not limited to, polyethylene glycol (PEG), branched PEG, PSA, mPSA, CA, mCA, carbohydrate, polysaccharides, pullulan, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC).

In particular embodiments of the invention illustrated in examples below, the water soluble polymer is PEG or branched PEG.

In further particular embodiments of the invention illustrated in examples below, the water soluble polymer is polysialic acid (PSA) or a modified PSA (mPSA). The PSA or mPSA may have a molecular weight range of 350 Da to 120,000 Da, 500 Da to 100,000 Da, 1000 Da to 80,000 Da, 1500 Da to 60,000 Da, 2,000 Da to 45,000 Da or 3,000 Da to 35,000 Da.

The PSA or mPSA may be colominic acid or modified colominic acid.

In another embodiment of the invention, the PSA or mPSA is comprised of about 5-500 or 10-300 sialic acid units. In yet another embodiment, the aforementioned method is provided wherein the oxidizing agent is sodium periodate ($NaIO_4$).

The method of the invention may comprise oxidizing the water soluble polymer to form an aldehyde group on a terminal sialic acid unit of the water soluble polymer, and reacting the oxidized water soluble polymer with an aminooxy linker.

In yet another embodiment of the invention, the aforementioned method is provided wherein the water soluble polymer is prepared by reacting an activated aminooxy linker with oxidized water soluble polymer wherein the linker is a homobifunctional or heterobifunctional linker. The homobifunctional linker can have the general formula $NH_2[OCH_2CH_2]_nONH_2$, wherein n=1-11, preferably 1-6. The linker may specifically be selected from:

a 3-oxa-pentane-1,5-dioxyamine linker of the formula:

and
a 3,6,9-trioxa-undecane-1,1'-dioxyamine linker of the formula:

PSA or mPSA may be oxidized by incubation with a oxidizing agent to form a terminal aldehyde group at the non-reducing end of the PSA.

The method may comprise oxidizing the water soluble polymer to form an aldehyde group on a terminal unit of the water soluble polymer, e.g. a terminal sialic acid unit of the PSA or mPSA, and reacting the oxidized water soluble polymer with an aminooxy linker. In still another embodiment, an aforementioned method is provided wherein the aminooxy linker is 3-oxa-pentane-1,5-dioxyamine. In a related embodiment, the oxidizing agent is $NaIO_4$.

In another embodiment of the invention, the aforementioned method is provided wherein the contacting of the oxidized carbohydrate moiety with the activated water soluble polymer occurs in a buffer comprising a nucleophilic catalyst selected from the group consisting of aniline and aniline derivatives.

In yet another embodiment of the invention, an aforementioned method is provided further comprising the step of reducing an oxime or hydrazone linkage in the conjugated protein, for example by incubating the conjugated protein in a buffer comprising a reducing compound selected from the group consisting of sodium cyanoborohydride ($NaCNBH_3$) and ascorbic acid (vitamin C). In a related embodiment the reducing compound is sodium cyanoborohydride ($NaCNBH_3$).

In another embodiment of the invention, a conjugated glycoprotein produced by any aforementioned method is provided. In still another embodiment of the invention, a conjugated glycoprotein other than a blood coagulation protein, a ganglioside or a drug delivery system comprises (a) the said glycoprotein, ganglioside or drug delivery system; and (b) at least one aminooxy water soluble polymer bound to the glycoprotein of (a), wherein said aminooxy water soluble polymer is attached to the glycoprotein, ganglioside or drug delivery system via one or more carbohydrate moieties. In a still further embodiment of the invention, a conjugated glycoprotein other than a blood coagulation protein, a ganglioside or a drug delivery system comprises (a) the said glycoprotein, ganglioside or drug delivery system; and (b) at least one hydrazide water soluble polymer bound to the glycoprotein of (a), wherein said hydrazide water soluble polymer is attached to the glycoprotein ganglioside or drug delivery system via one or more carbohydrate moieties.

DETAILED DESCRIPTION OF THE INVENTION

The pharmacological and immunological properties of carbohydrate-containing compounds, such as glycoproteins other than blood coagulations proteins can be improved by chemical modification and conjugation with water soluble polymer, in particular PEG or PSA or mPSA. The properties of the resulting conjugates generally strongly depend on the structure and the size of the polymer. Thus, polymers with a defined and narrow size distribution are usually preferred. PSA and mPSA, used in specific examples, can be purified in such a manner that results in a final PSA preparation with a narrow size distribution.

Glycoproteins

As described herein, glycoproteins other than blood coagulation proteins including, but not limited to cytokines such as interleukins, alpha-, beta-, and gamma-interferons, colony stimulating factors including granulocyte colony stimulating factors, fibroblast growth factors, platelet derived growth factors, phospholipase-activating protein (PUP), insulin, plant proteins such as lectins and ricins, tumor necrosis factors and related alleles, soluble forms of tumor necrosis factor receptors, interleukin receptors and soluble forms of interleukin receptors, growth factors, tissue growth factors, transforming growth factors such as TGFαs or TGFβs and epidermal growth factors, hormones, somatomedins, pigmentary hormones, hypothalamic releasing factors, antidiuretic hormones, prolactin, chorionic gonadotropin, follicle-stimulating hormone, thyroid-stimulating hormone, tissue plasminogen activator, and immunoglobulins such as IgG, IgE, IgM, IgA, and IgD, erythropoietin (EPO), blood factors other than blood coagulation proteins, galactosidases, α-galactosidases, β-galactosidases, DNAses, fetuin, fragments thereof, and any fusion proteins comprising any of the above mentioned proteins or fragments thereof together with therapeutic glycoproteins in general are contemplated by the invention.

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

An "analog," "variant" or "derivative" is a compound substantially similar in structure and having the same biological activity, albeit in certain instances to a differing degree, to a naturally-occurring molecule. For example, a polypeptide variant refers to a polypeptide sharing substantially similar structure and having the same biological activity as a reference polypeptide. Variants or analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence. By way of example, a "derivative" refers to a polypeptide sharing the same or substantially similar structure as a reference polypeptide that has been modified, e.g., chemically.

Variant or analog polypeptides include insertion variants, wherein one or more amino acid residues are added to a protein amino acid sequence of the invention. Insertions may be located at either or both termini of the protein, and/or may be positioned within internal regions of the protein amino acid sequence. Insertion variants, with additional residues at either or both termini, include for example, fusion proteins and proteins including amino acid tags or other amino acid labels. In one aspect, the protein molecule optionally contains an N-terminal Met, especially when the molecule is expressed recombinantly in a bacterial cell such as E. coli.

In deletion variants, one or more amino acid residues in a protein or polypeptide as described herein are removed. Deletions can be effected at one or both termini of the protein or polypeptide, and/or with removal of one or more residues within the protein amino acid sequence. Deletion variants, therefore, include fragments of a protein or polypeptide sequence.

In substitution variants, one or more amino acid residues of a protein or polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and are set out immediately below.

CONSERVATIVE SUBSTITUTIONS

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

CONSERVATIVE SUBSTITUTIONS II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Gangliosides

In embodiments, of the invention, gangliosides are conjugated to water soluble polymers, e.g. PEG or PSA or mPSA. Gangliosides are known to provide cells with distinguishing surface markers that can serve in cellular recognition and cell-to-cell communication. They are useful as therapeutic agents.

Conjugates of the invention may comprise a ganglioside and a water soluble polymer, in which the ganglioside comprises a glycosphingolipid (ceramide and oligosaccharide) with one or more sialic acids linked on the sugar chain. Gangliosides can be classified according to how many sialic acid units are present on the molecule. Examples of gangliosides are GM1, GM2 and GM3 (monosialo-gangliosides), GD1a, GD1b, GD2 and GD3 (disialo-gangliosides), GT1b (trisialo-ganglioside) and GQ1 (tetrasialo-ganglioside).

For use in the present invention, preferred gangliosides comprise a ceramide linked to glucose, which is linked to a first galactose, which is linked to N-acetylgalactosamine, which is linked to a second galactose. This second galactose can be linked to one sialic acid. The first galactose can be linked to one, two, three or four sialic acids. Sialic acids may be linked either as monomers (one on each of the galactose molecules), or as oligosialic acids (2-4 sialic acids) to the first galactose.

Where administered therapeutic gangliosides need to circulate in the blood for long periods. So that their action on target tissues is more effective, gangliosides can be polysialylated, for example, by the method of the invention.

Drug Delivery Systems

In further embodiments, of the invention, drug delivery systems are conjugated to a water soluble polymer, e.g. PEG or PSA or mPSA. In general, a drug delivery system (DDS) is any molecular or particulate entity which can control the fate and effect of drugs associated with the entity. DDSs can be separated into two general types. The first type comprises macromolecules (MDDSs), for instance antibodies, neoglycoproteins as well as synthetic polymers, such as poly (hydroxypropylmethacrylamide), polylysine and polymerised alkyl cyanoacrylates. The association of drugs with various types of macromolecular carriers, including monoclonal antibodies to target the drug to the desired sites is described for instance by Gregoriadis in Nature 265, 407-411 (1977). The second type is particulate DDSs (PDDSs), which comprises for instance nanospheres or microspheres, which comprise biodegradable materials such as albumin or semibiodegradable materials such as dextran and alkylcyanoacrylates polymers, or vesicles formed of nonionic surfactants or liposomes—for details of which see for example Gregoriadis in NIPS, 4, 146-151 (1989).

Drugs can either be covalently linked to, or passively entrapped into, the DDS. For instance, PDDS comprising surfactant vesicles or liposomes may entrap hydrophilic or hydrophobic pharmaceutically active compounds by being formed of an appropriate combination of layers of surfactant or lipid molecules. Pharmaceutically active compounds are usually covalently linked to MDDSs, by a bond which may or may not be lysed in the body, for instance before or after the active compound performs its function.

Many of the MDDSs have an intrinsic (e.g. antibodies) or acquired (e.g. neoglycoproteins) ability to be recognised by target cells or tissues through receptors on the latter's surface. Typically, such DDSs are taken up specifically by the target upon injection. Specific uptake is, however, limited with the bulk of the DDSs being taken up by other, irrelevant (to therapy) tissues. The reason for this is that antibodies and other DDS proteins (regardless of their specificity for the target) must be, like other proteins, catabolized at the end of their biological life.

Synthetic polymers used in the macromolecular type MDDSs are for instance poly(hydroxypropylmethacrylamide) polylysine and polymerised alkyl cyanoacrylates. These may be catabolized in the reticuloendothelial system (RES) or other tissues by appropriate lysosomal enzymes. It would be desirable to reduce the rate of catabolism of such biodegradable macromolecular type DDS by some means, for instance by reducing uptake of the DDS by the RES or other tissues, or by reducing degradation by lysosomal enzymes once taken up by the RES.

Particulate DDSs (PDDSs) are, as a rule, removed from the circulation by the RES. Because of their propensity for the RES, PDDSs are often used for the delivery of drugs to these tissues. It is often desirable however, that PDDSs are directed to tissues other than those of the RES. To achieve this goal, one must block or delay RES interception of PDDSs.

DDSs for use in the invention may not initially contain glycons. An option is to add or otherwise incorporate a glycon into the DDS structure. Examples of such cases are liposomes incorporating a mannosylated or a galactosylated lipid. These glycoliposomes will target actives to tissues which express a mannose or galactose receptor respectively.

Where DDSs need to circulate in the blood for long periods so that e.g. uptake by target tissues is more effective (as with hepatic parenchymal cells), they are advantageously polysialylated by the methods of the invention.

Administration

In one embodiment a conjugated compound of the present invention may be administered by injection, such as intravenous, intramuscular, or intraperitoneal injection.

To administer compositions comprising a conjugated compound of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a mammal having a clinically defined disorder.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

The present invention also relates to a pharmaceutical composition comprising an effective amount of a conjugated compound or protein as defined herein. The pharmaceutical composition may further comprise a pharmaceutically acceptable carrier, diluent, salt, buffer, or excipient. The pharmaceutical composition can be used for treating clinically-defined disorders. The pharmaceutical composition of the invention may be a solution or a lyophilized product. Solutions of the pharmaceutical composition may be subjected to any suitable lyophilization process.

As an additional aspect, the invention includes kits which comprise a composition of the invention packaged in a manner which facilitates its use for administration to subjects. In one embodiment, such a kit includes a compound or composition described herein (e.g., a composition comprising a conjugated protein), packaged in a container such as a sealed bottle or vessel, with a label affixed to the container or included in the package that describes use of the compound or composition in practicing the method. In one embodiment, the kit contains a first container having a composition comprising a conjugated protein and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

In one embodiment, the derivative retains the full functional activity of native therapeutic compounds, and provides an extended half-life in vivo, as compared to native therapeutic compounds. In another embodiment, the derivative retains at least 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native compound.

Sialic Acid and PSA

As used herein, "sialic acid moieties" includes sialic acid monomers or polymers ("polysaccharides") which are soluble in an aqueous solution or suspension and have little or no negative impact, such as side effects, to mammals upon administration of the PSA-protein conjugate in a pharmaceutically effective amount. PSA and mPSA are characterized, in one aspect, as having 1, 2, 3, 4, 5, 10, 20, 30, 40, 50, 60, 70, 80, 90, 100, 200, 300, 400, or 500 sialic acid units. In certain aspects, different sialic acid units are combined in a chain.

In one embodiment of the invention, the sialic acid portion of the PSA or mPSA compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally-occurring saccharide compounds, or introduced into derivative polysaccharide compounds. The PSA and mPSA used in the methods and conjugates of the invention may be further characterized as described above in the Background of the Invention.

The naturally occurring polymer PSA is available as a polydisperse preparation showing a broad size distribution (e.g. Sigma C-5762) and high polydispersity (PD). Because the polysaccharides are usually produced in bacteria carrying the inherent risk of copurifying endotoxins, the purification of long sialic acid polymer chains may raise the probability of increased endotoxin content. Short PSA molecules with 1-4 sialic acid units can also be synthetically prepared (Kang S H et al., Chem Commun. 2000; 227-8; Ress D K and Linhardt R J, Current Organic Synthesis. 2004; 1:31-46), thus minimizing the risk of high endotoxin levels. However PSA preparations with a narrow size distribution and low polydispersity, which are also endotoxin-free, can now be manufactured. Polysaccharide compounds of particular use for the invention are, in one aspect, those produced by bacteria. Some of these naturally-occurring polysaccharides are known as glycolipids. In one embodiment, the polysaccharide compounds are substantially free of terminal galactose units.

In various embodiments, the compound is linked to or associated with the PSA or mPSA compound in stoichiometric amounts (e.g., 1:1, 1:2, 1:3, 1:4, 1:5, 1:6, 1:7, 1:7, 1:8, 1:9, or 1:10, etc.). In various embodiments, 1-6, 7-12 or 13-20 PSA and/or mPSA units are linked to the compound. In still other embodiments, 1, 2, 3, 4, 5, 6, 7, 8, 9, 10, 11, 12, 13, 14, 15, 16, 17, 18, 19, 20 or more PSA and/or mPSA units are linked to the compound.

Optionally, the compound is modified to introduce glycosylation sites (i.e., sites other than the native glycosylation sites). Such modification may be accomplished using standard molecular biological techniques known in the art. Moreover, the compound, prior to conjugation via one or more carbohydrate moieties, may be glycosylated in vivo or in vitro.

Aminooxy Linkage

In one embodiment of the invention, the reaction of hydroxylamine or hydroxylamine derivatives with aldehydes (e.g., on a carbohydrate moiety following oxidation by sodium periodate) to form an oxime group is applied to the preparation of conjugates of compound. For example, a glycoprotein is first oxidized with a oxidizing agent such as sodium periodate ($NaIO_4$) (Rothfus J A et Smith E L., J Biol Chem 1963, 238, 1402-10; and Van Lenten L and Ashwell G., J Biol Chem 1971, 246, 1889-94). The periodate oxidation of e.g. glycoproteins is based on the classical Malaprade reaction described in 1928, the oxidation of vicinal diols with periodate to form an active aldehyde group (Malaprade L., Analytical application, Bull Soc Chim France, 1928, 43, 683-96). Additional examples for such an oxidizing agent are lead tetraacetate ($Pb(OAc)_4$), manganese acetate ($MnO(Ac)_3$), cobalt acetate ($Co(OAc)_2$), thallium acetate (TIOAc), cerium sulfate ($Ce(SO_4)_2$) (U.S. Pat. No. 4,367,309) or potassium perruthenate ($KRuO_4$) (Marko et al., J Am Chem Soc 1997, 119, 12661-2). By "oxidizing agent" a mild oxidizing compound which is capable of oxidizing vicinal diols in carbohydrates, thereby generating active aldehyde groups under physiological reaction conditions is meant.

The second step is the coupling of the polymer containing an aminooxy group to the oxidized carbohydrate moiety to form an oxime linkage. In one embodiment of the invention, this step can be carried out in the presence of catalytic amounts of the nucleophilic catalyst aniline or aniline derivatives (Dirksen A et Dawson P E, Bioconjugate Chem. 2008; Zeng Y et al., Nature Methods 2009; 6:207-9). The aniline catalysis dramatically accelerates the oxime ligation allowing the use of very low concentrations of the reagents. In another embodiment of the invention the oxime linkage is stabilized by reduction with $NaCNBH_3$ to form an alkoxyamine linkage.

In one embodiment of the invention, the reaction steps to conjugate PSA or mPSA to a protein are carried out separately and sequentially (i.e., starting materials (e.g., protein, polymer, etc), reagents (e.g., oxidizing agents, aniline, etc) and reaction products (e.g., oxidized carbohydrate on a protein, activated aminooxy polymer, etc) are separated between individual reaction steps).

Additional information on aminooxy technology can be found in the following references, each of which is incorporated in their entireties: EP 1681303A1 (HASylated erythropoietin); WO 2005/014024 (conjugates of a polymer and a protein linked by an oxime linking group); WO96/40662 (aminooxy-containing linker compounds and their application in conjugates); WO 2008/025856 (Modified proteins); Peri F et al., Tetrahedron 1998, 54, 12269-78; Kubler-Kielb J and Pozsgay V., J Org Chem 2005, 70, 6887-90; Lees A et al., Vaccine 2006, 24(6), 716-29; and Heredia K L et al., Macromoecules 2007, 40(14), 4772-9.

Advantages of the invention include high recovery of conjugate, high retention of activity of the conjugated glycoprotein compared to unconjugated protein and high conjugation efficiency.

The invention is now illustrated with reference to the following examples. Examples 1-3, 9 and 11-27 illustrate specific embodiments of the invention. Examples 4-8 and 10 are included as reference examples for their relevance to preparation of corresponding conjugates of the invention.

EXAMPLES

Example 1

Preparation of the Homobifunctional Linker $NH_2[OCH_2CH_2]_2ONH_2$

The homobifunctional linker $NH_2[OCH_2CH_2]_2ONH_2$

(3-oxa-pentane-1,5-dioxyamine) containing two active aminooxy groups was synthesized according to Boturyn et al. (Tetrahedron 1997; 53:5485-92) in a two step organic reaction employing a modified Gabriel-Synthesis of primary amines. In the first step, one molecule of 2,2-chlorodiethylether was reacted with two molecules of Endo-N-hydroxy-5-norbornene-2,3-dicarboximide in dimethylformamide (DMF). The desired homobifunctional product was prepared from the resulting intermediate by hydrazinolysis in ethanol. Except where otherwise specified, this is referred to as the diaminooxy linker in examples below.

Example 2

Preparation of the Homobifunctional Linker NH$_2$[OCH$_2$CH$_2$]$_4$ONH$_2$

The homobifunctional linker NH$_2$[OCH$_2$CH$_2$]$_4$ONH$_2$ (3,6,9-trioxa-undecane-1,11-dioxyamine) containing two active aminooxy groups was synthesized according to Boturyn et al. (Tetrahedron 1997; 53:5485-92) in a two step organic reaction employing a modified Gabriel-Synthesis of primary amines. In the first step one molecule of Bis-(2-(2-chloroethoxy)-ethyl)-ether was reacted with two molecules of Endo-N-hydroxy-5-norbornene-2,3-dicarboximide in DMF. The desired homobifunctional product was prepared from the resulting intermediate by hydrazinolysis in ethanol.

Example 3

Figure 2:
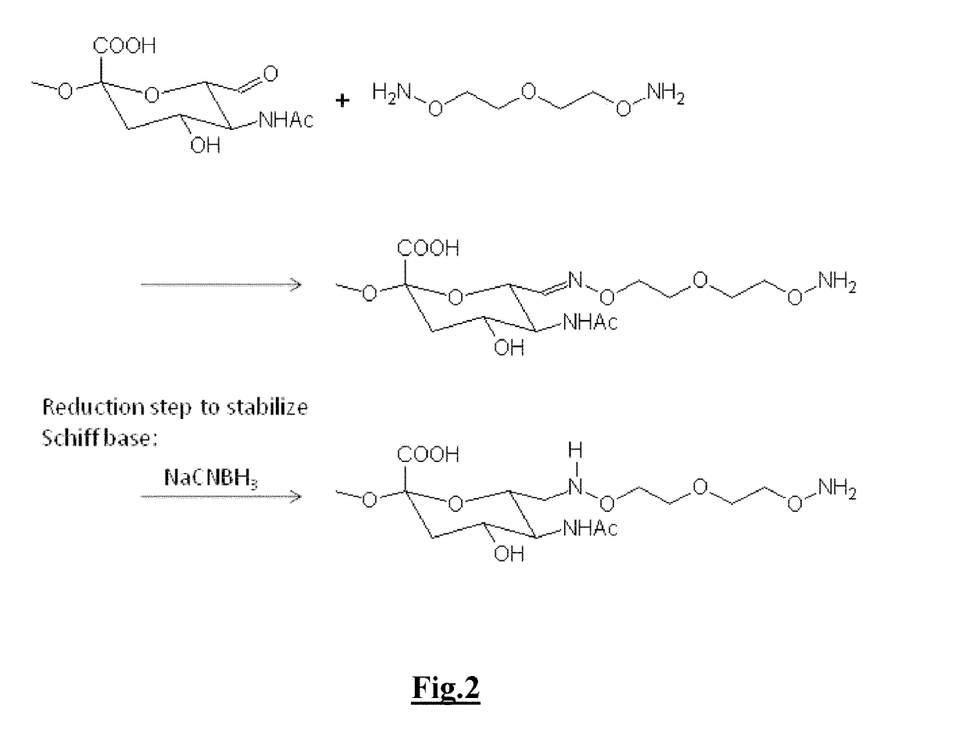
FIG. 2 shows the preparation of aminooxy-PSA.

Preparation of Aminooxy-PSA 500 mg of oxidized PSA (MW=18.8 kD) obtained from the Serum Institute of India (Pune, India) was dissolved in 8 ml 50 mM sodium acetate buffer, pH 5.5. Next, 100 mg 3-oxa-pentane-1,5-dioxyamine was added. After shaking for 2 hrs at room temperature, 44 mg sodium cyanoborohydride was added. After shaking for another 4 hrs at 4° C., the reaction mix was loaded into a Slide-A-Lyzer (Pierce, Rockford, Ill.) dialysis cassette (3.5 kD membrane, regenerated cellulose) and dialyzed against PBS pH 7.2 for 4 days. The product was frozen at −80° C. The preparation of the aminooxy-PSA according to this procedure is illustrated in FIG. 2.

Example 4

Coupling of aminooxy-PSA to rFIX and Purification of the Conjugate

To 12.6 mg rFIX, dissolved in 6.3 ml 50 mM sodium acetate buffer, pH 6.0, 289 μl of an aqueous sodium periodate solution (10 mM) was added. The mixture was shaken in the dark for 1 h at 4° C. and quenched for 15 min at room temperature by the addition of 6.5 μl 1 μM glycerol. Low molecular weight contaminates were removed by ultrafiltration/diafiltration (UF/DF) employing Vivaspin (Sartorius, Goettingen, Germany) concentrators (30 kD membrane, regenerated cellulose). Next, 43 mg aminooxy-PSA was added to the UF/DF retentate and the mixture was shaken for 18 hrs at 4° C. The excess PSA reagent was removed by hydrophobic interaction chromatography (HIC). The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted within 2.4 column volumes (CV) with 50 mM HEPES, 6.7 mM calcium chloride, 0.005% Tween 80, pH 7.4 at a flow rate of 5 ml/min. The preparation was analytically characterized by measuring total protein (BCA) and FIX chromogenic activity. For the PSA-rFIX conjugate a specific activity of 80.2 IU/mg protein was determined (56.4% in comparison to native rFIX). The results are summarized in Table 1.

TABLE 1

| Item | BCA [mg/ml] | FIX:Chrom [IU/ml] | Specific Activity [IU FIX:Chrom/mg BCA | Specific Activity [%] |
|---|---|---|---|---|
| rFIX | 8.58 | 1221 | 142.3 | 100 |
| PSA-rFIX | 1.15 | 92.2 | 80.2 | 56.4 |

Example 5

Coupling of Aminooxy-PSA to rFIX in the Presence of Aniline as Nucleophilic Catalyst To 3.0 mg rFIX, dissolved in 1.4 ml 50 mM sodium acetate buffer, pH 6.0, 14.1 μl of an aqueous sodium periodate solution (10 mM) was added. The mixture was shaken in the dark for 1 h at 4° C. and quenched for 15 min at room temperature by the addition of 1.5 μl 1 μM glycerol. Low molecular weight contaminates were removed by means of size exclusion chromatography (SEC) employing PD-10 desalting columns (GE Healthcare, Fairfield, Conn.). 1.2 mg oxidized rFIX, dissolved in 1.33 ml 50 mM sodium acetate buffer, pH 6.0 was mixed with 70 μl of aniline (200 mM aqueous stock solution) and shaken for 45 min at room temperature. Next, 4.0 mg aminooxy-PSA was added and the mixture was shaken for 2 hrs at room temperature and another 16 hrs at 4° C. Samples were drawn after 1 h, after 2 hrs and at the end of the reaction after 18 hrs. Next, excess PSA reagent and free rFIX were removed by means of HIC. The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted with a linear gradient to 50 mM HEPES, 6.7 mM calcium chloride, 0.005% Tween 80, pH 7.4 in 20 CV with at a flow rate of 5 ml/min.

Example 6

Coupling of Aminooxy-PSA to rFIX and Reduction with NaCNBH$_3$

To 10.5 mg rFIX, dissolved in 5.25 ml 50 mM sodium acetate buffer, pH 6.0, 53 μl of an aqueous sodium periodate solution (10 mM) was added. The mixture was shaken in the dark for 1 h at 4° C. and quenched for 15 min at room temperature by the addition of 5.3 μM glycerol. Low molecular weight contaminates were removed by means of UF/DF employing Vivaspin (Sartorius, Goettingen, Germany) concentrators (30 kD membrane, regenerated cellulose). Next, 35.9 mg aminooxy-PSA was added to the UF/DF retentate and the mixture was shaken for 2 hrs at room temperature. Then 53 μl of aqueous sodium cyanoborohydride solution (5M) was added and the reaction was allowed to proceed for another 16 hrs. Then the excess PSA reagent was removed by means of HIC. The conductivity of the cooled reaction mixture was raised to 180 mS/cm and loaded onto a 5 ml HiTrap Butyl FF HIC (GE Healthcare, Fairfield, Conn.) column (1.6×2.5 cm), pre-equilibrated with 50 mM HEPES, 3M sodium chloride, 6.7 mM calcium chloride, 0.01% Tween 80, pH 6.9. The conjugate was eluted within 2.4 CV with 50 mM HEPES, 6.7 mM calcium chloride, 0.005% Tween 80, pH 7.4 at a flow rate of 5 ml/min.

Example 7

Coupling of Aminooxy-PSA (Linker: NH$_2$[OCH$_2$CH$_2$]$_4$ONH$_2$) to rFIX and Purification of the Conjugate To 5.6 mg rFIX, dissolved in 2.8 ml 50 mM sodium acetate buffer, pH 6.0, 102 µl of an aqueous solution of sodium periodate (10 mM) was added. The mixture was shaken in the dark for 1 h at 4° C. and quenched for 15 min at room temperature by the addition of 2.9 µl of 1M glycerol. Low molecular weight contaminates were removed by means of UF/DF employing Vivaspin (Sartorius, Goettingen, Germany) concentrators (30 kD membrane, regenerated cellulose). Then 19 mg aminooxy-PSA was added to the UF/DF retentate and the mixture was shaken for 18 hrs at 4° C. The excess PSA reagent was removed by means of HIC. The conductivity of the cooled reaction mixture was raised to 180 mS/cm and loaded onto a 5 ml HiTrap Butyl FF (GE Healthcare, Fairfield, Conn.) HIC column (1.6×2.5 cm), pre-equilibrated with 50 mM HEPES, 3M sodium chloride, 6.7 mM calcium chloride, 0.01% Tween 80, pH 6.9. The conjugate was eluted within 2.4 CV with 50 mM HEPES, 6.7 mM calcium chloride, 0.005% Tween 80, pH 7.4 at a flow rate of 5 ml/min.

Example 8

Coupling of Aminooxy-PSA to rFVIII

To 11 mg rFVIII, dissolved in 11 ml Hepes buffer pH 6 (50 mM Hepes, 5 mM CaCl$_2$, 150 mM NaCl, 0.01% Tween) 57 µl 10 mM sodium periodate was added. The mixture was shaken in the dark for 30 min at 4° C. and quenched for 30 min at 4° C. by the addition of 107 µl of an aqueous 1M glycerol solution. Then 19.8 mg aminooxy-PSA (18.8 kD) was added and the mixture was shaken over night at 4° C. The ionic strength was increased by adding a buffer containing 8M ammonium acetate (8M ammonium acetate, 50 mM Hepes, 5 mM CaCl$_2$, 350 mM NaCl, 0.01% Tween 80, pH 6.9) to get a final concentration of 2.5M ammonium acetate. Next, the reaction mixture was loaded on a HiTrap Butyl FF (GE Healthcare, Fairfield, Conn.) column which was equilibrated with equilibration buffer (2.5M ammonium acetate, 50 mM Hepes, 5 mM CaCl$_2$, 350 mM NaCl, 0.01% Tween 80, pH 6.9). The product was eluted with elution buffer (50 mM Hepes, 5 mM CaCl$_2$, 0.01% Tween 80, pH 7.4), and the eluate was concentrated by centrifugal filtration using Vivaspin (Sartorius, Goettingen, Germany) devices with 30,000 MWCO.

Example 9

Preparation of the Homobifunctional Linker NH$_2$[OCH$_2$CH$_2$]$_6$ONH$_2$

The homobifunctional linker NH$_2$[OCH$_2$CH$_2$]$_6$ONH$_2$ (3,6,9,12,15-pentaoxa-heptadecane-1,17-dioxyamine) containing two active aminooxy groups was synthesized according to Boturyn et al. (Tetrahedron 1997; 53:5485-92) in a two step organic reaction employing a modified Gabriel-Synthesis of primary amines. In the first step one molecule of hexaethylene glycol dichloride was reacted with two molecules of Endo-N-hydroxy-5-norbornene-2,3-dicarboximide in DMF. The desired homobifunctional product was prepared from the resulting intermediate by hydrazinolysis in ethanol.

Example 10

Polysialylation of rFIX Employing a Maleimido/Aminooxy Linker System

A. Preparation of the modification reagent

An Aminooxy-PSA reagent is prepared by use of a maleimido/aminooxy linker system (Toyokuni et al., Bioconjugate Chem 2003; 14, 1253-9). PSA-SH (20 kD) containing a free terminal SH-group is prepared using a two step procedure: a) Preparation of PSA-NH$_2$ by reductive amination of oxidized PSA with NH$_4$Cl according to WO05016973A1 and b) introduction of a sulfhydryl group by reaction of the terminal primary amino group with 2-iminothiolane (Traut's reagent/Pierce, Rockford, Ill.) as described in U.S. Pat. No. 7,645,860. PSA-SH is coupled to the maleimido-group of the linker at pH 7.5 in PBS-buffer using a 10-fold molar excess of the linker and a PSA-SH concentration of 50 mg/ml. The reaction mixture is incubated for 2 hours under gentle shaking at room temperature. Then the excess linker reagent is removed and the aminooxy-PSA is buffer exchanged into oxidation buffer (50 mM sodium phosphate, pH 6.0) by diafiltration. The buffer is exchanged 25 times employing a Pellicon XL5 kD regenerated cellulose membrane (Millipore, Billerica, Mass.).

B. Modification of rFIX after Prior Oxidation with NaIO$_4$ rFIX is oxidized in 50 mM sodium phosphate buffer, pH 6.0 employing 100 µM sodium periodate in the buffer. The mixture was shaken in the dark for 1 h at 4° C. and quenched for 15 min at room temperature by the addition of glycerol to a final concentration of 5 mM. Low molecular weight contaminates were removed by means of size exclusion chromatography (SEC) employing PD-10 desalting columns (GE Healthcare, Fairfield, Conn.). Oxidized rFIX is then spiked with aniline to obtain a final concentration of 10 mM and mixed with the aminooxy-PSA reagent to achieve a 5 fold molar excess of PSA. The reaction mixture was incubated for 2 hours under gentle shaking in the dark at room temperature.

C. Purification of the Conjugates

The excess of PSA reagent and free rFIX is removed by means of HIC. The conductivity of the reaction mixture is raised to 180 mS/cm and loaded onto a column filled with 48 ml Butyl-Sepharose FF (GE Healthcare, Fairfield, Conn.) pre-equilibrated with 50 mM Hepes, 3 M sodium chloride, 6.7 mM calcium chloride, 0.01% Tween 80, pH 6.9. Subsequently the conjugate is eluted with a linear gradient of 60% elution buffer (50 mM Hepes, 6.7 mM calcium chloride, pH 7.4) in 40 CV. Finally the PSA-rFIX containing fractions are collected and subjected to UF/DF by use of a 30 kD membrane made of regenerated cellulose (Millipore). The preparation is analytically characterized by measuring total protein (BCA) and FIX chromogenic activity. For the PSA-rFIX conjugates prepared with both variants a specific activity of >50% in comparison to native rFIX was determined.

Example 11

Preparation of Aminooxy-PSA Reagent

An aminooxy-PSA reagent was prepared according to Example 3. The final product was diafiltrated against buffer, pH 7.2 (50 mM Hepes) using a 5 kD membrane (regenerated cellulose, Millipore), frozen at −80° C. and lyophilized. After lyophilization the reagent was dissolved in the appropriate volume of water and used for preparation of PSA-protein conjugates via carbohydrate modification.

Example 12

Figure 1:
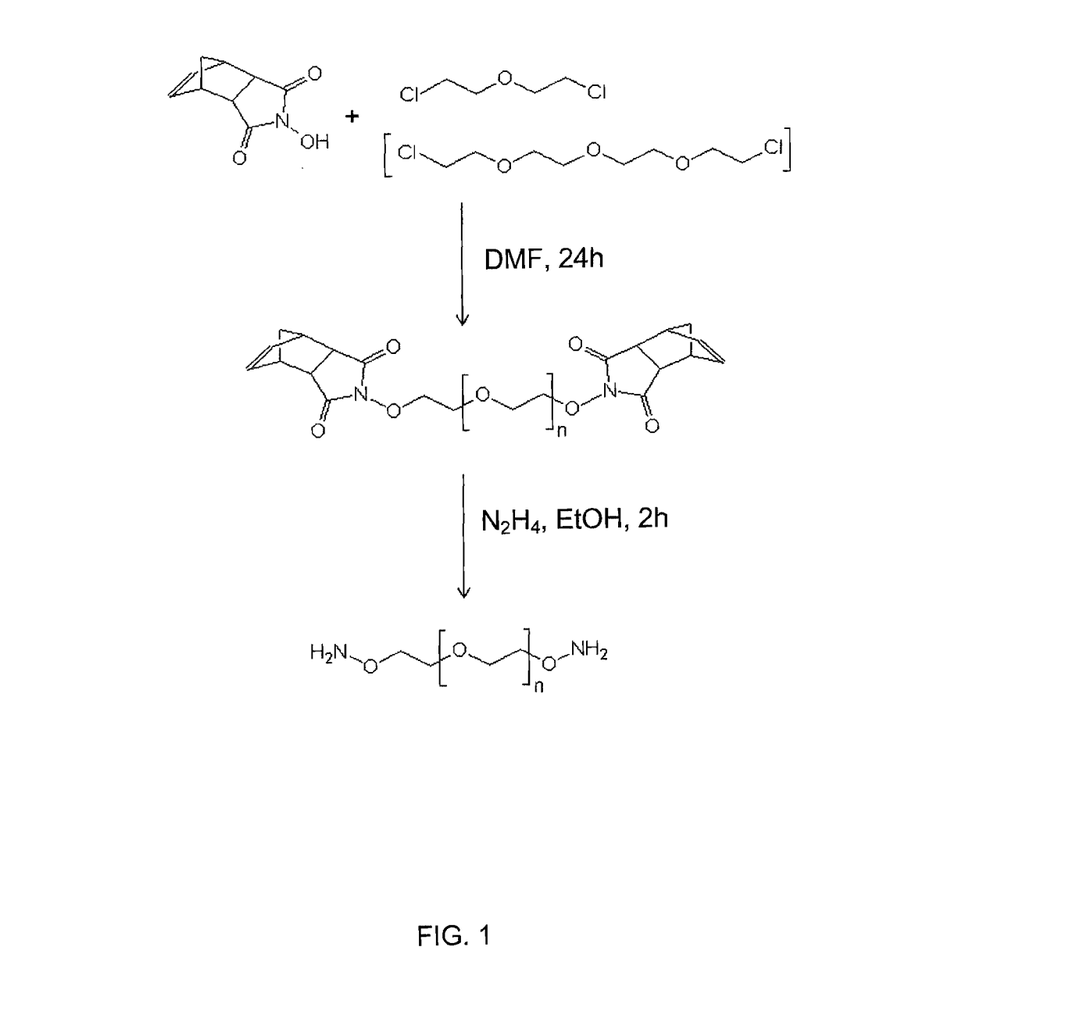
FIG. 1 shows the synthesis of the water soluble diaminoxy linkers 3-oxa-pentane-1,5-dioxyamine and 3,6,9-trioxa-undecane-1,1'-dioxyamine.

Detailed Synthesis of the Aminooxy-PSA Reagent 3-oxa-pentane-1,5 dioxyamine was synthesized according to Botyryn et al (Tetrahedron 1997; 53:5485-92) in a two step organic synthesis as outlined in Example 1.
Step 1:
To a solution of Endo-N-hydroxy-5-norbonene-2,3-dicarboximide (59.0 g; 1.00 eq) in 700 ml anhydrous N,N-dimethylformamide anhydrous $K_2CO_3$ (45.51 g; 1.00 eq) and 2,2-dichlorodiethylether (15.84 ml; 0.41 eq) were added. The reaction mixture was stirred for 22 hours at 50° C. The mixture was evaporated to dryness under reduced pressure. The residue was suspended in 2 L dichloromethane and extracted two times with saturated aqueous NaCl-solution (each 1 L). The Dichloromethane layer was dried over $Na_2SO_4$ and then evaporated to dryness under reduced pressure and dried in high vacuum to give 64.5 g of 3-oxapentane-1,5-dioxy-endo-2',3'-dicarboxydiimidenorbornene as a white-yellow solid (intermediate 1).
Step 2:
To a solution of intermediate 1 (64.25 g; 1.00 eq) in 800 ml anhydrous Ethanol, 31.0 ml Hydrazine hydrate (4.26 eq) were added. The reaction mixture was then refluxed for 2 hours. The mixture was concentrated to the half of the starting volume by evaporating the solvent under reduced pressure. The occurring precipitate was filtered off. The remaining ethanol layer was evaporated to dryness under reduced pressure. The residue containing the crude product 3-oxa-pentane-1,5-dioxyamine was dried in vacuum to yield 46.3 g. The crude product was further purified by column chromatography (Silicagel 60; isocratic elution with Dichloromethane/Methanol mixture, 9+1) to yield 11.7 g of the pure final product 3-oxa-pentane-1,5-dioxyamine.

Example 13

Preparation of Aminooxy-PSA Polymer 1.3 g of oxidized colominic acid (23 kDa) was dissolved in 18 ml of 50 mM sodium acetate pH 5.5±0.02. 20 fold molar excess of 1,11-diamino-3,6,9-trioxaundecane (also referred to as 3,6,9-trioxa-undecane-1,11-dioxyamine) was dissolved in minimum amount of 50 mM sodium acetate (pH 5.5±0.02) and was added to the PSA solution. The final colominic acid concentration was 62.5 mg/ml. This reaction mixture was incubated for 2±0.1 hr at 22±1.0° C. on a gentle mixer (22 oscillations per minute). After this, 0.65 ml of 160 mg/ml $NaCNBH_3$ solution was added to the above reaction mixture so as to make the final concentration of 5.00 mg/ml. This was incubated for 3.0±0.20 hours at 4.0±1.0° C. on a shaker (22 oscillations per minute) in a endotoxin free air tight container with enough headspace for mixing. For the purification, the sample was diluted with 2 mM triethanolamine, pH 8.0±0.02 to make final colominic acid concentration of 20 mg/ml. The reaction mixture was desalted to remove excess of 1,11-diamino-3,6,9-trioxaundecane, $NaCNBH_3$ and byproducts of the reaction. This was followed by desalting on a Sephadex G25 column using 20 mM triethanolamine buffer (pH 8.0±0.02). The pH of the desalted sample was adjusted to pH 7.8-8.0 and was ultrafiltered/diafiltered with 20 mM TEA pH 8.0 once and 2 mM triethanolamine (TEA) pH 8.0 twice. The sample was freeze dried and stored at −80° C.

Alternatively, purification was done in presence of high salt during desalting and ultrafiltration/diafiltration (UF/DF) steps. Anion exchange chromatography in high salt was also used to make highly pure aminooxy-PSA. Different molecular weights of aminooxy-PSA were synthesized.

Example 14

Coupling of Diaminooxy (3,6,9-trioxa-undecane-1,11-dioxyamine)-PSA to β-Galactosidase For oxidation of β-Galactosidase (β-Gal), different concentrations of $NaIO_4$ (ranging from 0.157 mM to 2 mM) were used. 0.5 mg of β-Gal was oxidized under acidic pH of 5.75 at 4° C. for 30 minutes in the dark. Oxidation was stopped by adding $NaHSO_3$ to a final concentration of 5 mM. The conjugation reaction was carried out using the oxidized β-Gal with diaminooxy PSA polymer (22 kDa). The final concentration of polymer in the reaction mixture was 1.25 mM whereas the concentration of β-Gal ranged from 0.125 mg/ml to 0.76 mg/ml. All the reactions were done at pH5.75. Sodium cyanoborohydride was added to the reaction mixture to a concentration of 50 mM or 3.17 mg/ml. The reaction was carried out at 4° C. and samples were collected at time intervals of 1, 2 and 24 hours. Conjugates were characterized using SDS PAGE and western blotting. A shift in the band was seen for the conjugate in SDS PAGE and this was also confirmed by western blotting.

Based on the best reactions conditions, 1.9 mg of β-Gal was oxidized with 1.5 mM of $NaIO_4$ for 30 minutes at 4° C. and then oxidation was stopped by adding $NaHSO_3$ to a final concentration of 5 mM. The conjugation reaction was carried out using the oxidized β-Gal with diaminooxy PSA polymer. The final concentrations of polymer and protein in the reaction mixture were 1.25 mM and 0.76 mg/ml respectively. The final pH of the reaction mixture was around 5.75. Sodium cyanoborohydride was added to the reaction mixture to a concentration of 50 mM or 3.17 mg/ml. The reaction was carried out at 4° C. for 2 hours. Purified and unpurified conjugates were characterized using SDS PAGE and western blotting. A shift in the band was seen for the conjugate in SDS PAGE and this was confirmed by western blotting using anti-PSA antibody. The in vitro activity PSA-βGal conjugates were comparable to native protein using All in one βGal assay kit (Pierce). Further, the overall process was scaled up to 3 fold.

Example 15

Coupling of Diaminooxy-PSA to Fetuin

Fetuin and was oxidized with 10 mM $NaIO_4$ for 60 minutes at 4° C. in the dark and the oxidation was stopped by adding NaHSO$_3$ to a final concentration of 10 mM. The conjugation reaction was carried out using the oxidized Fetuin with diaminooxy PSA polymer (23 kDa). The final concentration of polymer in the reaction mixture was 2.5 mM at pH 5.75. Sodium cyanoborohydride was added to the reaction mixture to a concentration of 50 mM or 3.17 mg/ml. The final protein concentration in the reaction was 0.714 mg/ml and the reaction was carried out at 4° C. for 2 hours. These conjugates were characterized using SDS PAGE and western blotting. A shift in the band was seen for the conjugates in SDS PAGE and this was also confirmed by western blotting.

For a scale up reaction, 5 mg Fetuin was oxidized with 10 mM NaIO$_4$ for 60 minutes at 4° C. in dark and then oxidation was stopped by adding NaHSO$_3$ to a final concentration of 10 mM. The conjugation reaction was carried out using the oxidized Fetuin with diaminooxy PSA polymer (23 kDa). The final concentration of polymer in the reaction mixture was 2.5 mM at pH of 5.75. Sodium cyanoborohydride was added to the reaction mixture to a concentration of 50 mM or 3.17 mg/ml. The reaction was carried out at 4° C. and sample was collected after 2 hours. Purified and unpurified conjugates were characterized using SDS PAGE and western blotting. A shift in the band was seen for the conjugate in SDS PAGE and this was also confirmed by western blotting.

Example 16

Coupling of Diaminooxy-PSA to Fetuin with Aniline to Act as a Nucleophilic Catalyst 0.2 mg of Fetuin was oxidized with 10 mM NaIO$_4$ for 30 minutes at 4° C. in dark and then oxidation was stopped by adding NaHSO$_3$ to a final concentration of 5 mM. The conjugation reaction was carried out using the oxidized Fetuin with diaminooxy PSA polymer (23 kDa). The final concentration of polymer in the reaction mixture was 1.25 mM. The final pH of reaction mixture was 5.75. Sodium cyanoborohydride was added to the reaction mixture to a concentration of 50 mM or 3.17 mg/ml. The final protein concentration in the reaction was 0.125 mg/ml. 84.21 µl of 200 mM aniline solution was added to the 1.6 ml of reaction mixture. The reaction was carried out at 4° C. overnight.

Example 17

Coupling of Diaminooxy-PSA to Erythropoietin (EPO)

0.2 mg of EPO was oxidized with 10 mM of NaIO$_4$ for 30 minutes at 4° C. The oxidation was stopped by adding NaHSO$_3$ to a final concentration of 5 mM. The conjugation reaction was carried out using the oxidized EPO with diaminooxy polymer of 23 kDa. The final concentration of polymer in the reaction mixture was 1.25 mM. The final concentration of EPO in the reaction mixture was 0.125 mg/ml. The final pH of the reaction mixture was around 5.75. Sodium cyanoborohydride was added to the reaction mixture to a concentration of 50 mM or 3.17 mg/ml. The reaction was carried out at 4° C. for 24 hours. Unpurified conjugate was characterized using SDS PAGE. A shift in the band was seen for the conjugate in SDS PAGE.

Example 18

Coupling of Diaminooxy-PSA to EPO with Aniline to act as a Nucleophilic Catalyst 0.2 mg of EPO was oxidized with 10 mM NaIO$_4$ for 30 minutes at 4° C. The oxidation was stopped by adding NaHSO$_3$ to a final concentration of 5 mM. The conjugation reaction was carried out using the oxidized EPO with diaminooxy PSA polymer (22 kDa). The final concentration of polymer in the reaction mixture was 1.25 mM. The final pH of the reaction mixture was around 5.75. Sodium cyanoborohydride was added to the reaction mixture to a concentration of 50 mM or 3.17 mg/ml. The final protein concentration in the reaction was 0.125 mg/ml. 84.21 µl of 200 mM aniline solution was added to the 1.6 ml of reaction mixture. The reaction was carried out at 4° C. for overnight. The conjugates were characterized using SDS PAGE. A shift in the band was seen in the conjugates. No adverse effect of aniline was observed on activity of the conjugates.

Example 19

Coupling of Diaminooxy-PSA to DNAse

For glycopolysialylation of DNAse, bovine pancreas DNAse was used for conjugation reaction. This source of DNAse was supplied as lyophilized powder, which was stored at −20° C. Prior to the reaction, this lyophilized powder was dissolved in sodium acetate buffer (pH 5.75). The polymer used for glycopolysialylation had a weight in the range of 10 kDa to 22 kDa. For oxidation of glycon moiety of DNAse, NaIO$_4$ was used as oxidizing agent to a final concentration of 1 mM. DNAse was oxidized at acidic pH of 5.75 at 4° C. for 30 minutes. The oxidation was stopped by adding NaHSO$_3$ to a final concentration of 2 mM. After oxidation was complete, the conjugation reaction was carried out by addition of diaminooxy PSA polymer to a final concentration of 1.25 mM. NaCNBH$_3$ was added to the reaction mixture to a final concentration of 50 mM or 3.17 mg/ml and the polysialylation of the DNAse was preformed 4.0±1.0° C. for at least 2 hours. The reactions were stopped with 25 molar excess of Tris over polymer. The conjugates were characterized using SDS PAGE and western blotting. A shift in the band was seen for the conjugate in SDS PAGE and positing result was obtained from western blotting. Activity was measured as 95% (compared with the less than 50% observed in comparable conjugates made using aldehyde linker chemistry).

Example 20

Coupling of Diaminooxy (3 oxa-pentane-1,5-dioxyamine linker)-PSA to β-Galactosidase For oxidation of β-Galactosidase, NaIO$_4$ was used at a concentration of 2 mM. 3 mg of β-Galactosidase was oxidized at acidic pH of 5.75 at 4° C. for 30 minutes then oxidation was stopped by adding NaHSO$_3$ to a final concentration of 2 mM. The conjugation reaction was carried out using the oxidized β-Galactosidase with diaminooxy PSA polymer (23 kDa). The final concentration of polymer in the reaction mixture was 1.5 mM. The final concentration of β-Galactosidase in reaction mixture was 0.867 mg/ml. The final pH of reaction mixture was around 5.75. Sodium cyanoborohydride was added to the reaction mixture to a concentration of 50 mM or 3.17 mg/ml. The reaction was carried out at 4° C. for 2 hours. Conjugates were characterized using SDS PAGE and western blotting. A shift in the band was seen for the conjugate in SDS PAGE and positing result was obtained from western blotting.

Example 21

Preparation of Hydrazine-Colominic Acid

We used the following protocol to prepare a PSA-hydrazide (colominic acid-hydrazide) using adipic acid dihydrazide. Analogous methods are used to make other PSA-hydrazides.
1 Dissolve 1 g of activated colominic acid in ~10 ml of 20 mM sodium acetate pH 5.5±0.02. Final colominic acid concentration should be 62.5 mg/ml
2 Dissolve 25-fold molar excess (over oxidized colominic acid "CAO") of adipic acid dihydrazide (MW=174.2 gms) in minimum amount of 20 mM sodium acetate (pH 5.5±0.02) and add to solution from 1.

3 Amount of adipic acid dihydrazide to be added $$= \frac{\text{Weight of } CAO \text{ in grams} \times 25 \times \text{MW of adipic acid dihydrazide in } gms}{\text{MW of } CAO \text{ in Daltons}}$$

$$= \frac{1 \times 25 \times 174.2}{15 \times 10^3}$$

$$= 0.290 \text{ g}$$

4 After adding adipic acid dihydrazide solution, make up the volume of colominic acid with sodium acetate to a final concentration of 62.5 mg/ml. Therefore total reaction volume is 16 ml.
5 Incubate the reaction mixture for 2±0.1 hr at 22.0±1.0° C. on shaker (22 oscillations per minute).
6 Prepare concentrated NaCNBH$_3$ solution (165 mg/ml) and add 0.5 ml to solution from 1 so that the final concentration of this becomes 5.0 mg/ml in the final reaction mixture. Incubate the reaction mixture for 3.0±0.20 hours at 4.0±1.0° C. on shaker (22 oscillations per minute).
7 Keep the reaction mixture in endotoxin-free, air tight container with excess 50 ml of headspace for proper mixing (there should be enough space so that reaction mixture should not touch the cap of container).
8 After 3 hours reaction at 4° C., dilute the sample with 2 mM triethanolamine (make the volume up to 50 ml), at pH 8.0±0.02 to make final colominic acid concentration to 20 mg/ml.
9 Desalt the reaction mixture to remove excess of untreated adipic acid dihydrazide, NaCNBH$_3$ etc from the polymer. This can be done by GPC (using XK 50 Sephadex G-25 medium matrix; ≤1.8 mg of CA/ml matrix; 35 cm bed height; Column volume=687 ml) by observing UV 224 nm and conductivity. Desalting is carried out with 20 mM triethanolamine (pH 8.0±0.02) buffer.
10 After desalting, colominic acid-hydrazide is subjected to 1 cycle of ultrafiltration, 1 cycle of diafiltration using 20 mM TEA, pH 8.0±0.02 and at least 3 cycles of diafiltration using 2 mM TEA, pH 8.0±0.02. This can be done using 3 kDa vivaflow cassettes.
11 Adjust the pH of desalted sample to pH 7.8-8.0. Optionally, freeze-dry the sample and consecutively keep it for secondary drying to remove excess of moisture.

Example 22

Coupling of Hydrazide-PSA to Erythropoietin

For oxidation of erythropoietin (EPO), NaIO$_4$ was used at a concentration of 10 mM. EPO (1 mg) was oxidized at pH 5.75 at 4° C. for 30 minutes then oxidation was stopped by adding NaHSO$_3$ to a final concentration of 5 mM. The conjugation reaction was carried out using the oxidized EPO with hydrazide-PSA polymer. The molecular weight of the hydrazide-PSA used for conjugation was 24.34 kDa. The final concentration of hydrazide-PSA in the reaction mixture was 1.25 mM. The final concentration of EPO in the reaction mixture was 0.125 mg/ml. The final pH of the reaction mixture was around 5.75. Sodium cyanoborohydride was added to the reaction mixture to a concentration of 50 mM or 3.17 mg/ml. The reaction was carried out at 4° C. for 24 hours. Conjugates were characterized using SDS PAGE and western blotting. A shift in the band was seen for the conjugate in SDS PAGE and a positive result was obtained from western blotting.

Example 23

Coupling of Hydrazide-PSA to β-Galactosidase

β-Galactosidase (0.5 to 4.5 mg) was oxidized with 0.625 to 2 mM of NaIO$_4$ for 30 minutes at 4° C. The oxidation was stopped by adding NaHSO$_3$ to a final concentration of 5 mM. The conjugation reaction was carried out using the oxidized β-galactosidase with hydrazide-PSA ranging from 24.34 kDa to 27.9 kDa. The final concentration of hydrazide-PSA in the reaction mixture was 1.25 mM. The final concentration of β-galactosidase in the reaction mixture was in a range from 0.125 mg/ml to 0.76 mg/ml. The final pH of reaction mixture should be around 5.75. Sodium cyanoborohydride was added to the reaction mixture to a concentration of 50 mM or 3.17 mg/ml. The reaction was carried out at 4° C. and samples were collected at 1, 2 and 24 hours. Purified and unpurified conjugate was characterized using SDS PAGE and western blotting. A shift in the band was seen for the conjugate in SDS PAGE and a positive result was obtained from western blotting. Activity was measured as 84%.

Example 24

Coupling of Hydrazide-PSA to Fetuin

Fetuin (0.25 mg) was oxidized with NaIO4 (5 or 10 mM) for 30 or 60 minutes at 4° C. The oxidation was stopped by adding NaHSO$_3$ to a final concentration of 5 or 10 mM as appropriate to match the concentration of NaIO$_4$ used for oxidation. The conjugation reactions were carried out using the oxidized Fetuin with adipic acid dihydrazide-PSA polymer. The final concentration of the polymer in the reaction mixture was between 1.25 and 2.5 mM. The final pH of reaction mixture was around 5.75. Sodium cyanoborohydride was added to the reaction mixture to a concentration of 50 mM or 3.17 mg/ml. The reaction was carried out at 4° C. for 1 hour to 4 hours. The conjugates were characterized using SDS PAGE and western blotting. A shift in the band was seen for the conjugate in SDS PAGE for each set of reaction conditions and a positive result was obtained from western blotting.

A scaled-up reaction for 5 mg Fetuin followed by purification of the resulting conjugate was carried out. 5 mg Fetuin was oxidized with 10 mM NaIO$_4$ for 60 minutes at 4° C. and then oxidation was stopped by adding NaHSO$_3$ to a final concentration of 10 mM. The conjugation reaction was carried out using the oxidized Fetuin with adipic acid dihydrazide-PSA polymer. The final concentration of polymer in the reaction mixture was 2.5 mM. The final pH of reaction mixture was around 5.75. Sodium cyanoborohydride was added to the reaction mixture to a concentration of 50 mM or 3.17 mg/ml. The reaction was carried out at 4° C. and samples were collected at 2 hours. Purified and unpurified conjugate was characterized using SDS PAGE and western blotting. A shift in the band was seen for the conjugate in SDS PAGE and a positive result was obtained from western blotting.

Example 25

Coupling of Hydrazide-PSA to DNAse

DNAse was oxidized with NaIO4 to a final concentration ranging from 0.2 mM to 2 mM for 30 minutes at 4° C. The oxidation reaction was stopped by adding NaHSO$_3$ to a final concentration of between 2 and 5 mM depending upon the concentration of NaIO$_4$ used for oxidation. Glycopolysialylation of oxidized DNAse was carried out by addition of hydrazide-PSA polymer to a final concentration of 1.25 mM to the oxidized DNAse. Sodium cyanoborohydride was added to the reaction mixture to a final concentration of 50 mM or 3.17 mg/ml and the glycopolysialylation of the DNAse was performed at 4° C. for a time period ranging from 1 hour to 2 hours. The reactions were stopped with 25-fold molar excess of Tris over polymer. The conjugates were characterized using SDS PAGE and western blotting. A shift in the band was seen for the conjugates in SDS PAGE and a positive result was obtained from western blotting. The activity was measured as 49%.

Example 26

PEGylation of β-Galactosidase using Aminooxy Linker (3-oxa-pentane-1,5-dioxyamine)

β-Galactosidase (1 mg) was oxidized with 1.5 mM of NaIO$_4$ for 30 minutes at 4° C. The oxidation was stopped by adding NaHSO$_3$ to a final concentration of 1.5 mM. The conjugation reaction was carried out using the oxidized β-Galactosidase with diaminooxy-PEG polymer (20 kDa). The final concentration of the polymer in the reaction mixture was 1.25 mM. The final concentration of β-Galactosidase in the reaction mixture was 1 mg/ml. The final pH of reaction mixture should be around 5.75. Sodium cyanoborohydride was added to the reaction mixture to a concentration of 50 mM or 3.17 mg/ml. The reaction was carried out at 4° C. for 2 hours. Unpurified conjugate was characterized using SDS PAGE and a shift in the band was seen for the conjugate in SDS PAGE. The activity was measured as 59%.

Example 27

PEGylation of Erythropoietin using Aminooxy Linker

Erythropoietin (EPO; 0.2 mg) was oxidised with 5 or 10 mM NaIO$_4$ in 50 mM sodium acetate at pH 5.75 for 45 minutes at 4° C. and then oxidation was stopped by adding NaHSO$_3$ to a final concentration of 5 or 10 mM (to match the concentration of NaIO$_4$ used for oxidisation). The conjugation reaction was carried out using the oxidised EPO with diaminooxy PEG polymer (20 kDa). The final concentration of the polymer in the reaction mixture was 1.5 mM. The final pH of reaction mixture should be around 5.75. Sodium cyanoborohydride was added to the reaction mixture to a concentration of 50 mM or 3.17 mg/ml. The final protein concentration in the reaction was 0.4 mg/ml. The conjugation reaction was carried out overnight at 4° C.

The invention thus provides conjugates of compounds other than blood coagulation proteins with water soluble polymers, in particular PSA and mPSA.

The invention claimed is:

1. A method of conjugating a polysialic acid (PSA) or a modified PSA (mPSA) to an oxidized carbohydrate moiety on a polypeptide with DNase activity, comprising contacting the oxidized carbohydrate moiety with the PSA or mPSA under conditions that allow conjugation,
    wherein said PSA or mPSA contains an aminooxy group and an oxime linkage is formed between the oxidized carbohydrate moiety and the aminooxy group on the PSA or mPSA; and
    wherein said polypeptide has a specific activity of at least 80% relative to an unmodified polypeptide.

2. The method of claim 1 wherein the PSA or mPSA is colominic acid or modified colominic acid.

3. The method of claim 1 wherein the PSA or mPSA comprises 10-300 sialic acid units.

4. The method of claim 1, further comprising oxidizing the carbohydrate moiety by incubating said polypeptide with sodium periodate (NaIO$_4$).

5. The method of claim 1, further comprising oxidizing the PSA or mPSA to form an aldehyde group on a terminal unit of the PSA or mPSA, and reacting the oxidized PSA or mPSA with an aminooxy linker.

6. The method of claim 5 comprising oxidizing the PSA or mPSA using NaIO$_4$.

7. The method of claim 1 wherein said contacting the oxidized carbohydrate moiety with PSA or mPSA occurs in a buffer comprising a nucleophilic catalyst selected from the group consisting of aniline and aniline derivatives.

8. The method of claim 1 wherein the aminooxy group is formed by reacting oxidized PSA or mPSA with an aminooxy linker selected from the group consisting of 3-oxa-pentane-1,5 -dioxyamine and 3,6, 9-trioxa-undecane-1, 11-dioxyamine.

9. The method of claim 1 further comprising reducing an oxime linkage said polypeptide by incubation in the presence of a reducing compound.

10. The method according to claim 9 wherein the reducing compound is sodium cyanoborohydride (NaCNBH$_3$) or ascorbic acid (vitamin C).

11. A conjugated polypeptide with DNase activity, comprising:
    (a) a polypeptide with DNase activity; and
    (b) at least one aminooxy-PSA or aminooxy-mPSA bound to the polypeptide of (a), wherein said aminooxy-PSA or aminooxy-mPSA is attached to the polypeptide via one or more oxidized carbohydrate moieties; and
    wherein said polypeptide has a specific activity of at least 80% relative to an unmodified polypeptide.

* * * * *